(12) United States Patent
Abbott et al.

(10) Patent No.: US 6,573,405 B1
(45) Date of Patent: Jun. 3, 2003

(54) IONIC LIQUIDS

(75) Inventors: Andrew P. Abbott, Leicester (GB); David L. Davies, Oadby (GB)

(73) Assignee: Scionix Limited, London (GB)

( * ) Notice: Subject to any disclaimer, the term of this patent is extended or adjusted under 35 U.S.C. 154(b) by 0 days.

(21) Appl. No.: 09/926,116

(22) PCT Filed: Mar. 23, 2000

(86) PCT No.: PCT/GB00/01090

§ 371 (c)(1),
(2), (4) Date: Sep. 24, 2001

(87) PCT Pub. No.: WO00/56700

PCT Pub. Date: Sep. 28, 2000

(30) Foreign Application Priority Data

Mar. 24, 1999 (GB) .............................................. 9906829

(51) Int. Cl.[7] ..................... C07C 211/65; C07C 215/40; C07C 219/06; C07B 37/12; C07B 37/04
(52) U.S. Cl. ........................................ 564/292; 564/296
(58) Field of Search ................................. 564/292, 296

(56) References Cited

U.S. PATENT DOCUMENTS

| | | | | |
|---|---|---|---|---|
| 4,764,440 A | | 8/1988 | Jones et al. ................... | 429/198 |
| 4,839,249 A | * | 6/1989 | Jones et al. ................... | 429/194 |
| 5,188,914 A | * | 2/1993 | Blomgren et al. ........... | 429/112 |
| 5,525,567 A | | 6/1996 | Chauvin et al. ............. | 502/162 |
| 5,552,241 A | * | 9/1996 | Mamantov et al. ......... | 429/103 |
| 5,731,101 A | | 3/1998 | Sherif et al. ................. | 429/102 |
| 5,847,174 A | | 12/1998 | Nakao ............................ | 556/1 |
| 5,892,124 A | | 4/1999 | Olivier et al. ............... | 568/374 |

FOREIGN PATENT DOCUMENTS

| | | |
|---|---|---|
| EP | 838447 | 4/1998 |
| EP | 852148 | 7/1998 |
| FR | 2611700 | 9/1988 |
| FR | 2626572 | 8/1998 |
| WO | WO95/21872 | 8/1995 |
| WO | WO01/55060 | 8/2001 |

OTHER PUBLICATIONS

Earle, M. J., et al., Green Chem. 1, 23–25 (2/99).
Earle, M. J., et al., Pure Appl. Chem. 72, No. 7, 1391–1398 (2000).
esp@cenet abstract of Koura, N., et al. JP 1095469 (4/89).
Lee, C. W., Tetrahedron Letters 40(13), 2461–2464 (1999).
Sitze, M. S., et al., Inorg. Chem. 40, 2298–2301 (2001).
Welton, T., Chem. Rev. 99, 2071–2083 (1999).
Fischer, T., et al., Tetrahedron Letters 40, 793–794 (1999).
Kitazume, T., et al., Green Chem. 3(1), 30–32 (2001)—abstract only.
Scheffler, T. B., et al. Proc., Electrochem. Soc. 90–17, 281–289 (1990)—abstract only.
Parshall, G. W., J. Am. Chem. Soc. 94, 8716–8719 (1972).
Wasserscheid, P., et al., Angew. Chem. Int. Ed 39, 3773–3789 (2000).
Toi, B., et al., Chemical Abstracts 52:19953f (1958).
Lukkari S., et al., Chemical Abstracts 70:53495a (1968).
Khan, M. A., et al., Can. J. Chem. 63, 2119–2122 (1985).
Khan, M. A., J. of Molecular Structure 145, 203–218 (1986).
Sewada, K., et al., Bull. Chem. Soc. Jpn. 71, 2109–2118 (1998).
Tanaka, K., et al., Mol. Cryst. Liq. Cryst. 277, 139–143 (1996).
Brezeanu, M., et al., Chemical Abstracts 85:13205a (1976).
Kajita, T., et al., Chemical Abstracts 110:110144x (1989).
Kristiansson, O., et al., Acta Chemica Scandinavica 51, 270–273 (1997).
Li, Q., et al., Crystal Engineering 1(2), 169–176 (1998).
Abstract of WO 01/55060, Aug. 2, 2001.
Jones, F. N., J. Org. Chem. 32, 1667–1668 (1967).
Negita, H., et al., Bull. Chem. Soc. Jpn. 54, 391–393 (1981).
Saito, S., et al., J. Am. Chem. Soc. 88(22), 5107–5112 (1996).

* cited by examiner

*Primary Examiner*—Brian Davis

(57) ABSTRACT

An ionic liquid having a melting point of no more than 60° C., formed by the reaction of a quaternary ammonium compound of the formula:

$$R^1R^2R^3R^4N^+X^- \quad \text{(I)}$$

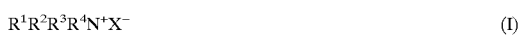

or a mixture of two or more therof;

with a halide of zinc, tin or iron, or a mixture of two or more thereof.

20 Claims, 2 Drawing Sheets

IONIC LIQUIDS

CROSS-REFERENCE TO RELATED APPLICATION

This is a filing under 35 U.S.C. 371 of PCT/GB00/01090, filed Mar. 23, 2000, which claims priority from United Kingdom Application No. 9906829.8, filed Mar. 24, 1999. PCT/GB00/01090 has been published under No. WO 00/56700, and the publication is in English.

This invention relates to ionic compounds and methods for their preparation In particular the invention relates to ionic compounds which are liquid at relatively low temperatures, i.e. generally below about 100° C., and preferably below about 60° C. and more preferably which are liquid at or near to ambient temperature.

There is much current interest in the field of ionic liquids. Such systems, which are examples of molten salts, have a number of interesting and useful chemical properties, and have utility, for example, as highly polar solvents for use in preparative chemistry, and as catalysts. They also have particular application in electrochemistry, for example in batteries, fuel cells, photovoltaic devices and electrodeposition processes, for example in baths for the electroplating of metals.

Ionic liquids have very low vapour pressure and thus, in contrast to many conventional solvents, are very advantageous in that they produce virtually no hazardous vapours. They are therefore advantageous from a health, safety and environmental point of view.

One such system which has been known for many years is that formed from 1-ethyl-3-methylimidazolium chlorides-aluminum chloride (EMIC—AlCl$_3$). This system is a thermally stable liquid between −100° C. to ca. 200° C., defendant on the molar ratio of EMIC to AlCl$_3$ utilised.

Such EMIC—AlCl$_3$ systems have been used extensively as solvents for various ionic reactions and as electrolytes, as described, for example in U.S. Pat. No. 5,525,567, FR-A-261170, FR-A-2626572, WO95/21872, and EP-A-838447 There are a number of difficulties in utilising such compounds. These arise principally from their cost, and from their water sensitivity.

In recent years, other ionic compounds have been made which are liquid at relatively low temperatures. For example, U.S. Pat. No. 4,764,440 discloses low temperature molten compositions, formed by reacting, for example, trimethylphenylammonium chloride with aluminum trichloride. The resulting ionic compound has a low freezing point (around −75° C.), but suffers from the same water sensitivity as EMIC—AlCl$_3$, because of the presence of aluminium trichloride.

Proposals have been made to utilise other metal halides, in place of aluminum trichloride. For example, U.S. Pat. No. 5,731,101 discloses the use of iron and zinc halides as the anion portion of an ionic liquid composition. The cation portion is formed by an amine hydrohalide salt, of the formula R$_5$ N.H.X. This reference indicates however that the aluminum compounds are preferred, and indeed contains comparative examples which indicate that it is not possible to substitute SnCl$_4$ for aluminium trichloride. Furthermore, it does not suggest the use of quaternary ammonium compounds as cations.

FR-A-2757850 (equivalent to U.S. Pat. No. 5,892,124) discloses liquid salts of the general formula Q$^+$A$^−$, wherein Q$^+$ represents quaternary ammonium or phosdhonium, and A$^−$ represents a various anions including tetrachloro- aluminate, and trichlorozincate. It is suggested that such compounds are useful as vehicles for carrying out Diels-Alder reactions.

We have now found that by forming the anion of an ionic compound from a halide of zinc, tin, or iron, and the carson from certain specific quaternary ammonium compounds, it is possible to produce compounds which are liquid at relatively low temperatures (i.e. below 60° C.), relatively inexpensive, and relatively water insensitive.

SUMMARY OF INVENTION

Accordingly, in a first aspect of the invention, there is provided an ionic compound having a melting point of no more than 60° C., formed by the reaction of a quaternary ammonium compound of the formula

$$R^1R^2R^3R^4N^-X \qquad (I)$$

or a mixture of two or more thereof;

with a halide of zinc, tin or iron, or a mixture of two or more thereof;

wherein R$^1$, R$^2$, and R$^3$, are each independently a C$_1$ to C$_5$ alkyl or a C$_6$ to C$_{10}$ cycloalkyl group, or wherein R$^2$ and R$^3$ taken together represent a C$_4$ to C$_{10}$ alkylene group, thereby forming with the N atom of formula I a 5 to 11-membered heterocyclic ring, and wherein R$^4$, is a C$_6$ to C$_{12}$ alkyl or a cycloalkyl group, or a C$_1$ to C$_{12}$ alkyl or a cycloalkyl group substituted with at least one group selected from OH, Cl, Br, F, I, NH$_3$, CN, NO$_2$, OR$^5$, COOR$^5$, CHO, and COR$^5$ wherein R$^5$ is a C$_1$ to C$_{10}$ alkyl or cycloalkyl group, and X as a suitable counter-ion.

The halide of zinc, tin or iron is preferably SnCl$_2$, ZnCl$_2$ or FeCl$_3$, and it is generally found that the most favourable freezing point Is obtained when the molar ratio of the quaternary ammonium compound to the zinc, tin, or iron halide is from 1:1.5 to 1:2.2, preferably about 1:2.

A particularly surprising finding is that very low melting points can be obtained by employing as the anionic component a mixture of halides selected from zinc, tin, and iron, for example a mixture of ZnCl$_2$ with SnCl$_2$.

The quaternary ammonium compounds (I) used in the preparation of the ionic compounds according to the invention are asymmetric, in that they have at least one substituent group (R$^4$) which is different from the remaining groups (R$^1$, R$^2$ and R$^3$). R$^4$ is preferably a C$_1$ to C$_{10}$ alkyl or a cycloalkyl group, substituted with at least one group selected from OH, Cl, Br, F, I, NH$_3$, CN, NO$_2$, OR$^5$, COOR$^5$, CHO, and COR$^5$. It is particularly preferred that R$^4$ is an ethyl group, substituted with one or more of hydroxyl, chlorine, or an ester (i.e. that the substituent R$^4$ is derived from choline, chlorocholine, or a chlorocholine ester). Specific examples of R$^4$ groups which have been found to be suitable are 2-hydroxyethyl, 2-bromoethyl, 2-chloroethyl, 2-acetoethyl, N-decyl, cyclohexyl, 2-hydroxy 3-chloropropyl, and 3-bromopropyl.

The counter-ion X$^−$ of compound (I) is preferably a halide, for example bromide or chloride, and will generally be the same halide as employed in the zinc, tin, or iron halide.

The ionic compounds according to the invention may be prepared simply by mixing together the quaternary ammonium compound (I), and the zinc, tin, or iron halide. The reaction is generally endothermic, and is usually carried out by heating, for example to a temperature of 100° C. or more. No additional solvent is generally employed, although it may be advantageous in some circumstances to carry out the reaction in a solvent which is an ionic liquid, in particular, an ionic liquid in accordance with the invention.

The ionic compounds according to the invention may be utilised for a wide range of purposes, for example as electrolytes in electrochemical devices such as batteries or fuel cells, in photovoltaic or electrochromic devices, and in electrochemical deposition or electro-refining. The compounds find particular application for carrying out applications where a polar but non-aqueous solvent is required. They may also be employed as inert media, for dissolving ionic species such as transition metal complexes, and, either alone, or after complexing with other metal ions, as catalysts, or as chemical reagents.

Figure 1:
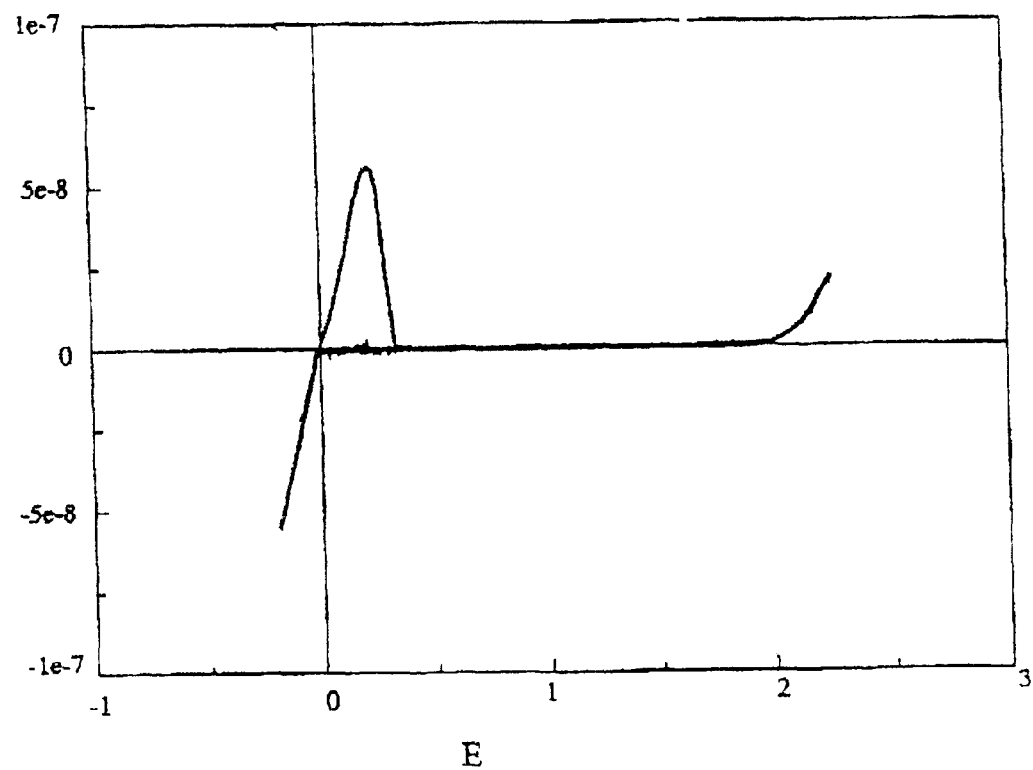
FIG. 1 is a cyclic voltammagram of an ionic liquid according to the invention.

A number of preferred embodiments of the invention are illustrated in the following examples. The composition of all of the products was characterised using mass spectroscopy.

EXAMPLE 1

A quaternary ammonium compound (choline chloride 1.40 g (0.01 mole)) was added to a metal halide ($ZnCl_2$ 2.72 g (0.02 mole)) in a laboratory test tube. The mixture was heated to a temperature of 120° C. for a period of 20 minutes to give a pale yellow liquid.

EXAMPLES 2 TO 21

Example 1 was repeated, using various quaternary ammonium halides, having the substituents shown in Table 1, in a molar ratio of 1:2 as in Example 1. In each case, an ionic compound was prepared which was liquid at temperatures above 60° C. The melting points of the compounds were determined, and are shown in Table 1. The melting process is often very slow, and was not in all cases measured to the highest possible level of accuracy. However, in all cases the melting point was determined to be no more than 60° C.

EXAMPLE 22

Example 1 was repeated, using as the quaternary ammonium compound 2-hydroxyethyl methyl piperidinium chloride ("hmpc") in place of choline chloride, in the same molar proportion. The melting point of the resulting salt was less than 23° C.

EXAMPLES 23 AND 24

Example 22 was repeated using $SnCl_2$ (0.02 moles) in place of $ZnCl_2$ (Example 23) and using a mixture of $ZnCl_2$ alone. (0.01 mole) and $SnCl_2$ (0.01 mole) in place of $SnCl_2$ alone. Both products had a melting point of less than 23° C.

EXAMPLE 25

Example 22 was repeated using a mixture of choline chloride, acetyl choline chloride (($CH_3)_3NC_2H_5OOCMe$), and $ZnCl_2$, in a molar ratio of 1:1:4. A clear liquid was produced with a melting point of less than 23° C.

EXAMPLE 26

The effect of molar ratio on melting point was investigated, by repeating Example 1, using various molar ratios of choline to ZnCl. The results are shown in

TABLE 1

| Example | $R^1$ | $R^2$ | $R^3$ | $R^4$ | Metal halide | Approximate Melting Point ° C. |
|---|---|---|---|---|---|---|
| 2 | Me | Me | Me | $C_2H_4Cl$ | $ZnCl_2$ | 24 |
| 3 | Me | Me | Me | $C_2H_4Br$ | $ZnCl_2$ | 24 |
| 4 | Me | Me | Me | $C_2H_4OOCMe$ | $ZnCl_2$ | 31 |
| 5 | Me | Me | Me | $C_2H_4OH$ | $ZnCl_2$ | 36 |
| 6 | Me | Me | Me | $CH_2CHOHCH_2Cl$ | $ZnCl_2$ | 37 |
| 7 | Me | Me | Me | $C_3H_7$ | $ZnCl_2$ | 46 |
| 8 | Me | Me | Me | $C_3H_6Br$ | $ZnCl_2$ | 23 |
| 9 | Me | Me | Me | $C_2H_4NH_2.HCl$ | $ZnCl_2$ | 58 |
| 10 | Me | Me | Me | $C_5H_{12}N^+ (CH_3)_3$ | $ZnCl_2$ | 46 |
| 11 | Me | Me | Me | $C_{10}H_{21}$ | $ZnCl_2$ | 48 |
| 12 | Et | Et | Et | $C_6H_{13}$ | $ZnCl_2$ | 56 |
| 13 | Me | Me | Me | $C_6H_{13}$ | $ZnCl_2$ | 43 |
| 14 | Me | Me | Me | $C_{12}H_{25}$ | $ZnCl_2$ | 42 |
| 15 | Me | Me | Me | $C_2H_4OOCMe$ | $ZnBr_2$ | 48 |
| 16 | Me | Me | Me | $C_2H_4OOCMe$ | $ZnCl_2$ | 31 |
| 17 | Me | Me | Me | $C_2H_4OOCMe$ | $SnCl_2$ | 20 |
| 18 | Me | Me | Me | $C_2H_4OH$ | $ZnBr_2$ | 38 |
| 19 | Me | Me | Me | $C_2H_4OH$ | $FeCl_3$ | 48 |
| 20 | Me | Me | Me | $C_2H_4OH$ | $SnCl_2$ | 37 |
| 21 | Me | Me | Me | $C_2H_4OH$ | $ZnCl_2:SnCl_2$ (1:1 molar ratio) | 6 |

TABLE 2

| Molar ratio choline: $ZnCl_2$ | 1:1 | 1:1.5 | 1:2 | 1:3 | 1:4 |
|---|---|---|---|---|---|
| Melting point ° C. | 63 | 60 | 36 | 43 | 73 |

EXAMPLE 27

Preparation of 2:1 Zinc Chloride-choline Chloride Ionic Liquids

An ionic liquid was prepared from anhydrous zinc chloride (98%—Sigma-Aldrich Limited) and [(2-hydroxyethyl)-trimethylammonium chloride] (99%—Sigma-Aldrich Limited). The zinc chloride and choline chloride, in a molar ratio of 2:1 were placed inside a glass beaker and heated to 120° C. During the melting stage the reactants were gently stirred. The time required for the complete formation of 10 grams of ionic liquid (i.e. no solid material) was approximately 25 minutes.

EXAMPLE 28

Electrochemical and Chemical Properties of 2:1 Zinc Chloride-choline Chloride Ionic Liquid The temperature dependence of the ionic Liquid Prepared in Example 27 was determined with the aid of a Jenway 4071 Conductivity Meter and Conductivity Probe. The probe cell constant was 1.2. The probe was immersed in the ionic liquid contained in a sample tube which in turn was suspended in an oil bath. The ionic liquid was heated to different temperatures and the resulting conductance values were recorded. The results obtained are shown in Table 3.

TABLE 3

| Temperature/° C. | Conductivity/$\mu Scm^{1}$ |
|---|---|
| 35.6 | 28.8 |
| 42.1 | 54.4 |
| 54.3 | 105.6 |
| 63.3 | 175.7 |
| 69.8 | 237.5 |
| 73.4 | 255.1 |
| 84.9 | 385.2 |
| 96.4 | 604.8 |
| 110.4 | 794.4 |

The chemical composition of the 2:1 zinc chloride-choline chloride ionic liquid was studied using mass spectroscopy. The instrument used in this study was a Kratos Concept Sector Mass Spectrometer equipped with negative ion fast atom bombardment (FAB). FAB mass spectra were obtained by introducing a small amount of the ionic liquid into the sample chamber and bombarding it with $Ar^+$ ions accelerated by a potential of 4 kV. The resulting spectra showed that the most stable complex zinc ions are $[ZnCl_3]^-$ (m/z 171), $[Zn_2Cl_5]^-$ (m/z 307) and $[Zn_3Cl_7]^{31}$ (m/z 443). NMR spectroscopy showed that the choline cation remains unchanged in the ionic liquid.

EXAMPLE 29

Zinc Electrodeposition

A 2:1 zinc chloride-choline chloride ionic liquid (4.12 grams) was prepared by the method described in Example 27, and poured into a boiling tube held in an oil bath at 60° C. Voltammetry was performed using a 10 $\mu$m diameter platinum working electrode (polished with 0.3 $\mu$m alumina paste) at Pt wire counter electrode and a zinc wire reference electrode. A PGSTAT20 Potentiostat controlled by GPES software was used to carry out the cyclic voltammetry. The results of this study is shown in FIG. 1.

FIG. 1 shows that the ionic liquid has a potential window of 2.02 V. The potential window is limited by zinc deposition and chlorine gas evolution at low and high potentials respectively.

The effect of current density on Zinc deposition was investigated, using a Hull cell. The structure of the Hull cell enables the deposition of a metal at a range of current densities to be obtained on a single cathode. A schematic diagram of the Hull cell employed is shown in is FIG. 2.

Figure 2:
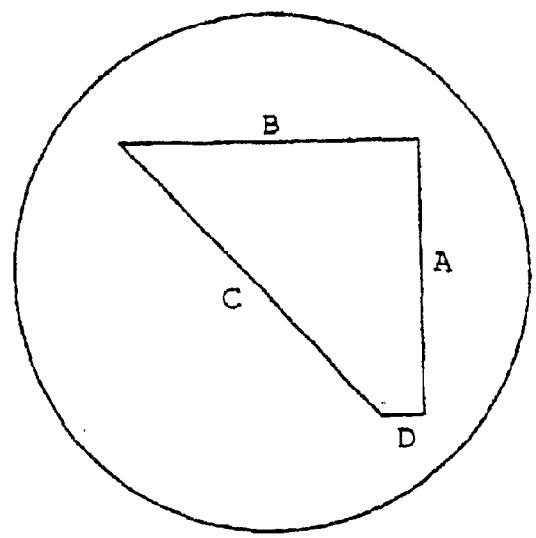
FIG. 2 is a schematic diagram of a Hull cell for the deposition of a metal.

To demonstrate zinc deposition an ionic liquid was prepared as above and poured into a Hull cell as shown in FIG. 2, having dimensions A=4.0 cm B=5.0 cm C=5.3 cm D=1.3 cm to a depth of approximately 1 cm.

A mild steel plate, 52 mm by 42 mm and 0.5 mm thick, was gently abraded with glass paper, cleaned with acetone and flame annealed. The mild steel plate was then placed inside the Hull cell along edge C. A nickel plate, 42 mm by 37 mm and 1 mm thick cleaned in a similar fashion was placed inside the cell along edge A. The Full cell was then suspended in a water bath set to a temperature so as to maintain the ionic liquid at 60° C. The temperature of the liquid was checked with a Jenway 4071 Conductivity Meter and Temperature Probe. Zinc deposition was achieved by connecting the mild steel and the nickel plates to the negative and positive terminals of a Thurlby Thander power pack respectively. In order to monitor accurately the current flowing in the circuit an ISO-TECH IDM 66 Digital Voltammeter was connected in series. For this demonstration a current of 3 mA was maintained for 2 hours. The potential required fluctuated between 15.65V and 14.02V.

After 2 hours the mild steel was removed from the Hull cell, washed with acetone and dried. Analysis of the plate revealed that a thick grey/white homogenous deposit was obtained with current densities between 0.47 $mAcm^{-2}$ and 0.29 $mAcm^{-2}$. A thinner whiter deposit was obtained with current densities between 0.29 $mAcm^{-2}$ and 0.21 $mAcm^{-2}$. Below 0.21 $mAcm^{-2}$ the zinc deposit was faint and non homogenous.

The corrosion resistance afforded by zinc plating from 2:1 zinc chloride-choline chloride was assessed by two methods. In the first, mild steel that had been partially coated with zinc was held approximately 5 cm above a 10% salt solution. For this study the salt solution was heated to 70° C. The unprotected regions began to rust after approximately 40 minutes and after 2 hours there was extensive rusting. The mild steel protected by zinc remained completely rust free.

In the second method an electrochemical technique was used to determine the effectiveness of zinc plating. A 1 mm diameter iron electrode was polished with alumina paste down to 0.3 mm. Together with a polished platinum electrode and a saturated calomel reference electrode (SCE) the iron electrode was immersed in 50 ml of an aqueous 0.1M potassium nitrate solution. The potential of the iron electrode was swept from −1V to 1V versus SCE at 20 $mVs^{-1}$. The result is shown in FIG. 3, in which curve A shows the current arising from iron oxidation.

The iron electrode was then cleaned, dried and immersed in a zinc chloride-choline chloride liquid, prepared according to the method of Example 27, in a boiling tube. Using a platinum electrode as a counter and zinc wire as a reference, zinc was deposited onto the iron at −0.45V versus zinc for 1 hour. The deposition was performed at 60° C. The iron electrode was then removed from the liquid, washed with acetone, dried and reimmersed in 0.1 M potassium nitrate solution. As before the potential of the iron electrode was swept from −1V to 1V versus SCE at 20 $mVs^{-1}$. The two scans are also shown in FIG. 3 Curve A is a plot of current I versus Potential E, for the iron electrode in an aqueous 0.1 M potassium nitrate solution and Curve B is for the same electrode electroplated with zinc.

Figure 3:
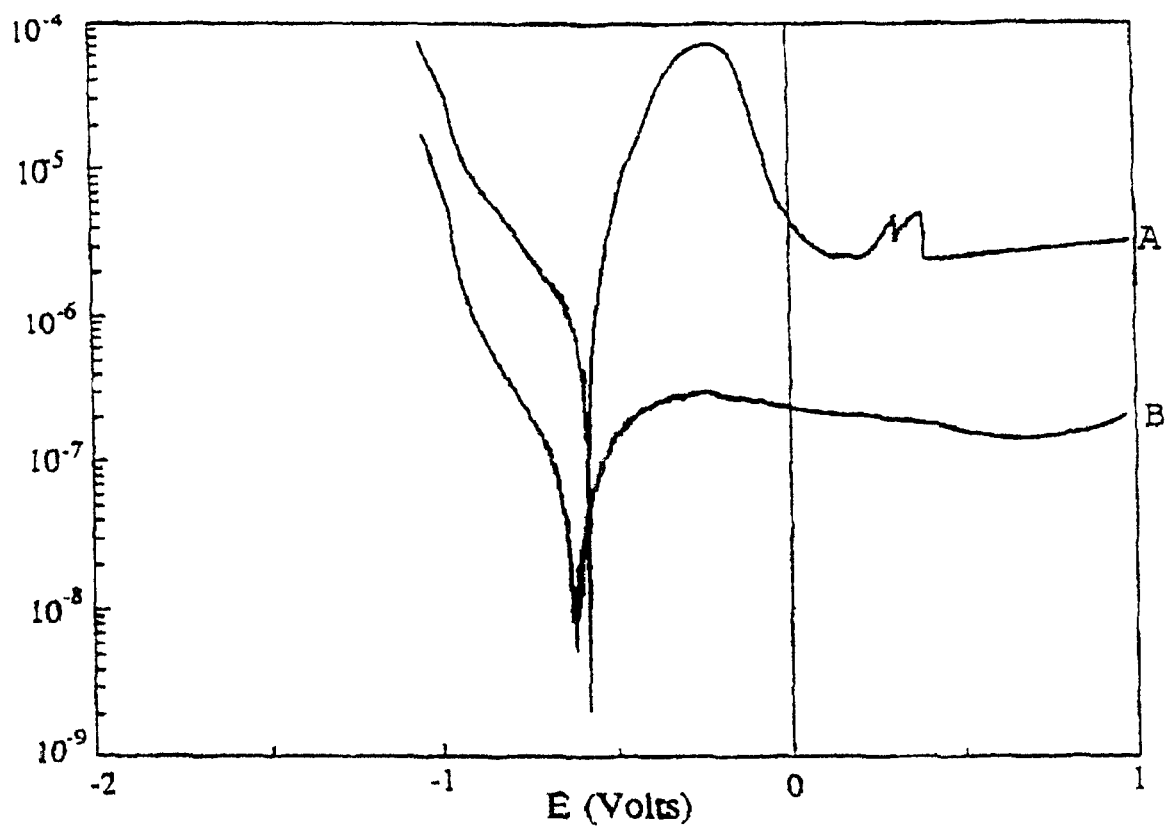
FIG. 3 is a current v potential curve for an electrode plated using a compound according to the invention.

From FIG. 3 it can be seen that zinc plating has reduced the corrosion current by approximately two orders of magnitude.

EXAMPLE 30

Zinc and Tin Co-deposition

In this experiment zinc and tin were deposited simultaneously onto mild steel. The materials used to prepare the ionic liquid used was 0.076 moles of zinc chloride, 0.004 moles of tin (II) chloride and 0.04 moles of choline chloride. The amount of tin(II) chloride present in the liquid was 4.5% by weight. The liquid was prepared in a beaker and poured into the Hull cell which was suspended in a water bath set to a temperature so as to maintain a temperature of 60° C. As before, mild steel and nickel were cleaned, placed inside the Hull cell and connected to the power pack in a similar fashion. For zinc-tin plating a current of 2.5 mA was maintained for 2 hours. The potential required was 11.36 V. The mild steel was then removed from the Hull cell, washed, dried and analysed. EDX analysis confirmed the presence of tin and zinc thus showing that both metals can be co-deposited. The deposit obtained was grey and darker than the pure zinc deposit. There was also less variation with current density. Between 0.39 mA cm$^{-2}$ and 0.18 mA cm$^{-2}$ the deposit was smooth and homogenous. Below 0.18 mA cm$^{-2}$ the deposit was fainter and less homogenous. At a current density of 0.25 mA cm$^{-2}$ the deposit contained approximately 80% Sn and 20% Zn

EXAMPLE 31

Electrochromics

A silver salt (silver nitrate or silver chloride) was dissolved in zinc-based ionic liquid and subsequently plated onto low resistance ITO glass. The time taken to darken the glass, remove the deposited silver, the voltage and current required and the reversibility of the process were determined. Zinc chloride (0.07 moles) and choline chloride (0.035 moles) were heated together at 90 C. in a beaker to give a clear colourless melt. The melt was then heated to 150° C. and 0.05 grams of silver chloride (0.35% per weight) was dissolved into it. The silver-containing melt was transferred to a sample tube suspended in an oil bath at 60° C. Low resistance ITO glass (13 mm by 66 mm) and copper foil (13 mm by 66 mm) were then immersed in the melt to a depth of approximately 1.5 cm. The copper and ITO glass were held parallel to each other and 1 cm apart. Zinc wire was used as a reference. Using a PGSTAT 20 Potentiometer, silver was deposited onto the ITO glass at −0.75 V versus zinc. The current that flowed was approximately 1.1 mA and total silver coverage was achieved in 257 seconds. The silver was then redissolved at 1.8 V versus zinc and the ITO glass became transparent after 124 seconds. In subsequent tests the silver plating and stripping times fell to approximately 2 minutes and 1.5 minutes respectively.

EXAMPLE 32

Dissolution of Metal Oxides

The 2:1 zinc chloride-choline chloride ionic liquid also has applications in metal oxide processing and metal recovery. Ruthenium, an important industrial catalyst, that has become spent may be reprocessed in the zinc ionic liquid. Spent ruthenium catalyst, in which the ruthenium is present as the oxide was used as a starting material for the following experiment. A small amount of the spent catalyst was dissolved in 12.37 g of the zinc-based ionic liquid contained in a sample tube at 90° C. to give A dark blue solution. The sample tube was then suspended in an oil bath at 60° C. A polished nickel flag (negative electrode, 0.5 cm$^{-2}$), a platinum flag (positive electrode) and a zinc wire reference electrode were immersed in the liquid A potential of 0.15 V was then applied for 2 hours (the resulting current was approximately 1.4 mA), after which time the nickel flag was removed, washed and analysed. The results of EDX analysis revealed the presence of electrodeposited ruthenium on the nickel flag.

EXAMPLE 33

Battery

Anhydrous ionic liquids prepared from metal chlorides and choline chloride can be used as electrolytes in batteries. Two ionic liquids were prepared, 2:1 zinc chloride-choline chloride and 2:1 iron (III) chloride-choline chloride. 2 ml of each at 90° C. were poured into separated compartments of a small glass cell. The compartments were separated by glass frit. The cell was suspended in an oil bath at 60° C. and zinc and carbon electrodes were immersed in the zinc and iron-based ionic liquids respectively. A Voltmeter was used to measure the resulting potential difference—the maximum recorded value was 1.47 V. The half cell reactions for this battery are;

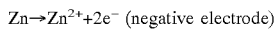

$Zn \rightarrow Zn^{2+}+2e^-$ (negative electrode)

and,

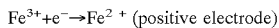

$Fe^{3+}+e^- \rightarrow Fe^{2+}$ (positive electrode)

EXAMPLE 34

Diels-Alder Reaction in Zinc Chloride-Choline Chloride (2:1) Ionic Liquid

General procedure for Diels-Alder reactions: A mixture of diene (0.012 mol) and dienophile (0.012 mol) in ZnCl$_2$-Choline chloride (2:1) ionic liquid (0.5 ml) was stirred mechanically or irradiated in an ultrasonic bath (reaction time as given below) and pure cycloaddduct was separated. For the majority of reactions further purification was not necessary but whenever appropriate flash column chromatography was used for further purification.

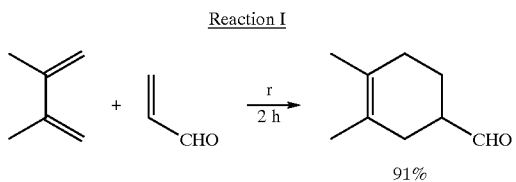

Reaction I $\delta 9.67$(s, 1H, CHO), 2.46(m, 1H, CHCHO), 2.12–1.81(m, 5H, 2×CH$_2$, CHH), 1.55(s, 3H, Me), 1.5(s, 3H, Me) and 1.53(m, 1H, CHH) according to the method of Odenkirk, W.; Rheingold, A. L.; Bosnich, B., *J. Am. Chem. Soc.,* 1992, 114, 6392.

After having separated out the cycloadduct and washed the ionic liquid with hexane, the remaining catalyst showed comparable catalytic activity in the melt in the five following reactions.

EXAMPLE 35

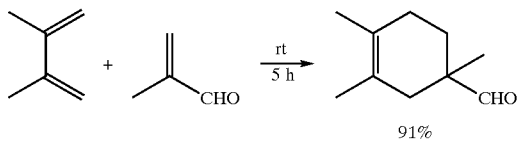

Reaction II $\delta 9.46$(s, 1H, CHO), 2.25–1.38(m, 6H, 3×CH$_2$), 1.62(s, 3H, Me), 1.58(s, 3H, Me) and 1.01(s, 3H, Me). (Baldwin, J. E. and Lusch, M. J., *J. Org. Chem.,* 1979, 44. 1923.)

EXAMPLE 36

Reaction III

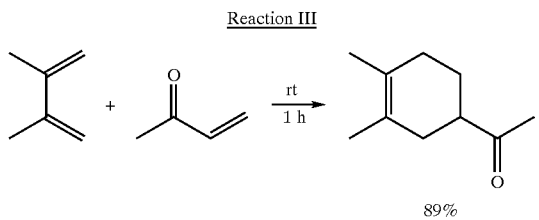

89%

δ2.55(m, 1H, C<u>H</u>Me), 2.18(s, 3H, Me), 2.15–1.84(m, 4H, 2×CH$_2$), 1.57(bs, 6H, 2×Me) and 1.57–1.42(m, 2H, CH$_2$). (Crabtree, R. H. and Davis, M. H., *J. Org. Chem.,* 1986, 51, 2655.)

EXAMPLE 37

Reaction IV

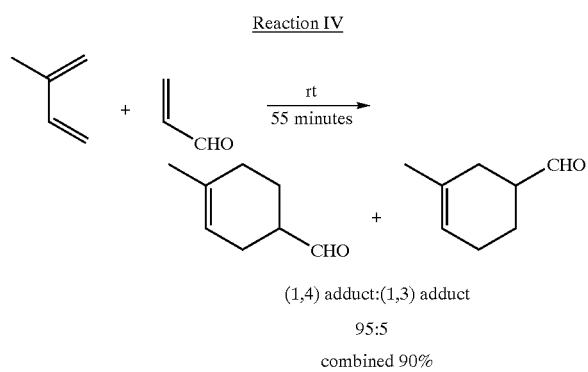

(1,4) adduct:(1,3) adduct

95:5 combined 90%

(1,4) adduct: δ9.69(d, 1H, J 1.15 Hz, CHO), 5.4(m, 1H, HC=C), 2.46(m, 1H, C<u>H</u>CHO), 2.21–1.6(m, 6H, 3×CH2) and 1.65(s, 3H, Me). (Bonnesen, P. V.; Puckett, C. L.; Honeychuck, R. V. and Hersh, W. H., *J. Am. Chem. Soc.,* 1989, 111, 6070.)

EXAMPLE 38

Reaction V

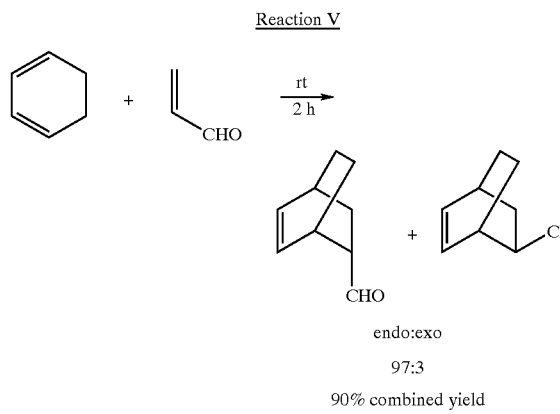

endo:exo

97:3

90% combined yield endo adduct: δ9.45(d, 1H, J 1.3 Hz, CHO), 6.33(dt, 1H, J 0.9 and 7.5 Hz, HC=C), 6.11(dt, 1H, J 0.9 and 7.5 Hz, HC=C)2.94(m, 1H, aliphatic-H), 2.54(m, 1H, alphatic-H) and 1.7–1.1(m, 6H. aliphatic-H). (Krantz, A. and Lin, C. Y., *J. Am. Chem. Soc.,* 1973, 95, 5662.)

EXAMPLE 39

Reaction VI

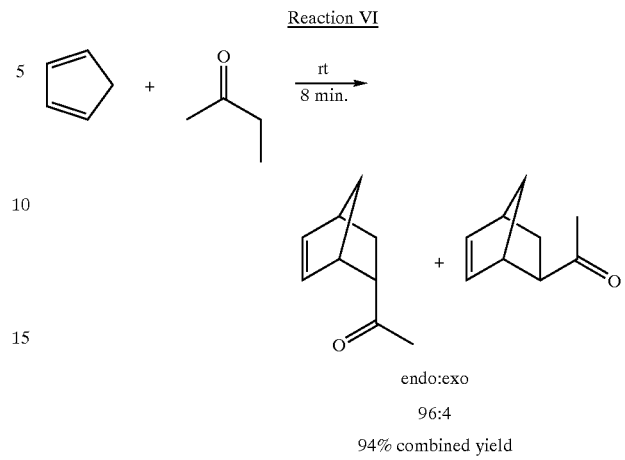

endo:exo

96:4

94% combined yield endo adduct: δ6.14(m, 1H, HC=), 5.86)m, 1H, HC=), 3.25(bs, 1H, CH), 3.0(m, 1H, <u>H</u>CCHO), 288(bs, 1H, CH), 2.1(s, 3H, Me), 1.5–1.4(m, 3H, CH$_2$ and C<u>H</u>H) and 1.31(d, 1H, J 8.8 Hz, CH<u>H</u>). (Stork, G and Guthikonda, R. N., *Tetrahedron Lett.,* 1972, 13, 2755)

EXAMPLE 40

Friedel-Crafts Reactions in ZnCl$_2$-Choline Chloride (2:1) Ionic Liquid

General procedure for Friedel-Crafts reactions: A mixture o aromatic compound (0.01 mol) and acid chloride (0.02 mol) in a ZnCl$_2$-Choline chloride (2:1) ionic liquid (melt) (0.5. ml) was stirred mechanically (reaction time as stated below) and acylated product was separated from DCM, dried (MgSO$_4$) and purified by flash column chromatography.

Reaction VI

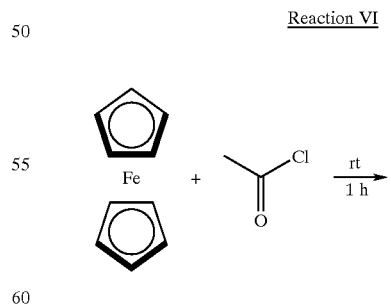

75%

4.76(dd, 2H, J 1.8 Hz, ArH), 4.5(dd, 2H, J 1.8 Hz, ArH), 4.2(s, 5H. ArH) and 2.4(s, 3H. Me). (Stark, A.; MacLean, B. L.; Singer, R. D., *J. Chem. Soc., Dalton Trans.,* 1999, 163.)

EXAMPLE 41

Reaction VII

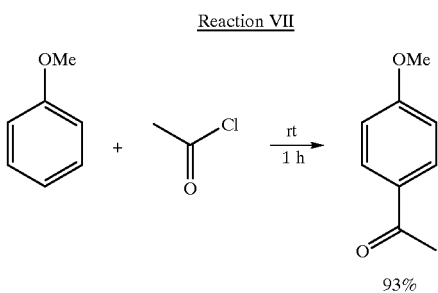

7.9(d, 2H, J 8.2 Hz, ArH), 6.8(d, 2H, J 8.2 Hz, ArH), 3.9(s, 3H, Ome) and 2.58(s, 3H, COMe). (Fasco, R. and Sannicolo, F., *J. Org. Chem.*, 1981, 46, 83.)

EXAMPLE 42

Reaction VIII

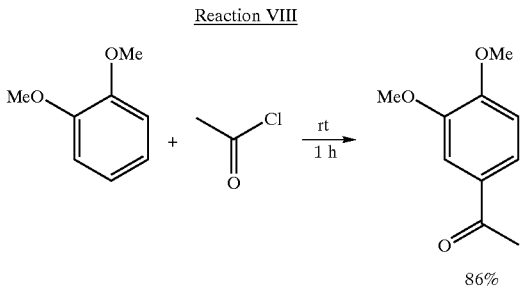

7.58(dd, 1H, J 1.8 and 8.4 Hz, ArH), 7.52(d, 1H, J 1.8 Hz, ArH), 6.86(d, 1H, J 8.4 Hz, ArH), 3.9(s, 6H, 2×Me) and 2.58(s, 3H, Me). (Tilley, J. W.; Clader, J. W.; Zawoiski, S.; Wirkus, M. and Le Mahieu, R. A., *J. Med. Chem.*, 1989, 32, 1814)

EXAMPLE 43

Mukaiyama Aldol Reaction in ZnCl$_2$-Choline Chloride (2:1) Melt

A mixture of phenyl trimethoxy ethylene (0.005 mol) and benzaldehyde (0.005 mol) in ZnCl$_2$-Choline chloride (2:1) melt (0.5 ml) was stirred mechanically for 10 minutes and silylated intermediate was pipetted out and treated with HCl(1N)/MeOH (1:10) to give pure 3-hydroxy 1,3-diphenyl-1-propanone quantitatively.

Reaction IX

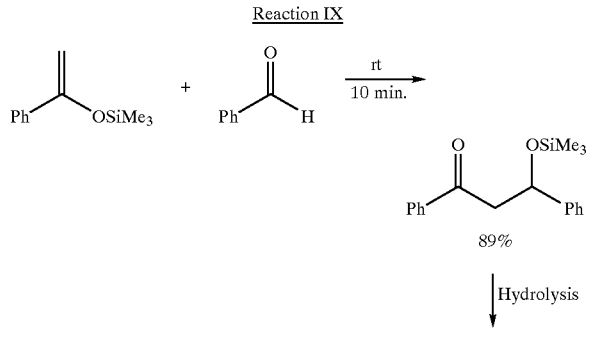

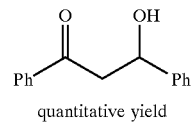

quantitative yield

Silylated intermediate: δ8.25–7.8(m, 2H, ArH), 7.5–7.2 (m, 8H, ArH), 5.4(dd, 1H, J 4 and 8.5 Hz, CHPh), 3.57(dd, 1H, J 8.5 and 15.5 Hz, C$\underline{H}$H), 3.0(dd, 1H, J 4 and 15.5 Hz, CH$\underline{H}$) and 0.03(s, 9H, 3×Me). (Le Roux, C.; Gaspard-Iloughmane, H. and Dubac, J., *J. Org. Chem.*, 1993, 58, 1835.)

3-hydroxy 1,3-diphenyl-1-propanone: δ8.2–7.0(m, 10H, ArH), 5.4–5.0(td, 1H, J 6.0 and 2.5 Hz, C$\underline{H}$OH), 3.43(1H, bs, OH) and 3.16(d, 2H, J 6 Hz, COCH$_2$). (House, H. O.; Crumrine, D. S.; Teranishi, A. Y. and Olmstead, H. D., *J. Am. Chem. Soc.*, 1973, 95, 3310.)

The foregoing Examples illustrate that the compounds according to the invention have utility in a wide range of applications, as solvents, and as electrolytes and components of batteries and electrolytic cells.

It will be apparent to one of skill in the art based on the properties apparent from the foregoing examples that a wide range of other applications are possible for the compounds according to the invention.

What is claimed is:

1. An ionic compound having a melting point of no more than 60° C., formed by the reaction of a quaternary ammonium compound or the formula $$R^1R^2R^3R^4N^+X^- \quad (I)$$

or a mixture of two or more thereof;

with a halide of zinc, tin or iron, or a mixture of two or more thereof;

wherein $R^1$, $R^2$, and $R^3$, are each independently a $C_1$ to $C_5$ alkyl or a $C_6$ to $C_{10}$ cycloalkyl group, or wherein $R_2$ and $R_3$ taken together represent a $C_4$ to $C_{10}$ alkylene group, thereby forming with the N atom of formula I a 5 to 11-membered heterocyclic ring, and wherein $R^4$, is a $C_6$ to $C_{12}$ alkyl or a cycloalkyl group, or a $C_1$ to $C_{12}$ alkyl or a cycloalkyl group substituted with at least one group selected from OH, Cl, Br, F, I, NH$_2$, CN, NO$_2$, COOR$^5$, CHO, COR$^5$ and OR$^5$, wherein $R^5$ is a $C_1$ to $C_{10}$ alkyl or cycloalkyl group, and X$^-$ is a suitable counter-ion.

2. An ionic compound as claimed in claim 1, wherein the halide of zinc, tin or iron is SnCl$_2$, ZnCl$_2$, ZnBr$_2$, or FeCl$_3$.

3. An ionic compound according to claim 1, wherein the molar ratio of the quaternary ammonium salt to the Zn, Sn or Fe halide is about 1 to 2.

4. An ionic compound as claimed in claim 1, wherein the said halide is a mixture of halides of Zn, Sn or Fe.

5. An ionic compound as claimed in claim 4, wherein the said halide is a mixture of halides of ZnCl$_2$ and SnCl$_2$.

6. An ionic compound as claimed in claim 1, wherein $R^4$ is a $C_1$ to $C_{10}$ alkyl or a cycloalkyl group, substituted with at least one group selected from OH, Cl, Br, F, I, NH$_2$, CN, NO$_2$, COOR$^5$, COR$^5$, CHO and OR$^5$, wherein $R^5$ is a $C_1$ to $C_{10}$ alkyl or cycloalkyl group.

7. An ionic compound as claimed in claim 1, wherein each of $R^1$, $R^2$, $R^3$, independently is a $C_1$ to $C_5$ alkyl or a cycloalkyl group.

8. An ionic compound as claimed in claim 7, wherein each of $R^1$, $R^2$, $R^3$, independently is methyl, ethyl or butyl.

9. An ionic compound as claimed in claim 8, wherein $R^1$, $R^2$, $R^3$, are each methyl, $R^1$, $R^2$, $R^3$, are each ethyl, or $R^1$, $R^2$, $R^3$, are each butyl.

10. An ionic compound as claimed in claim 1, wherein $R^1$, $R^2$, $R^3$, and $R^4$ have the following meaning:

| $R^1$ | $R^2$ | $R^3$ | $R^4$ |
|---|---|---|---|
| Me | Me | Me | $C_2H_4Cl$ |
| Me | Me | Me | $C_2H_4Br$ |
| Me | Me | Me | $C_2H_4OOCMe$ |
| Me | Me | Me | $C_2H_4OH$ |
| Me | Me | Me | $CH_2CHOHCH_2Cl$ |
| Me | Me | Me | $C_3H_7$ |
| Me | Me | Me | $C_3H_6Br$ |
| Me | Me | Me | $C_2H_4NH_2$ |
| Me | Me | Me | $C_5H_{12}N^+ (CH_3)_3$ |
| Me | Me | Me | $C_{10}H_{21}$ |
| Et | Et | Et | $C_6H_{13}$ |
| Et | Et | Et | $C_{12}H_{25}$. |

11. An ionic compound as claimed in claim 1, of one of following formulae

| $R^1$ | $R^2$ | $R^3$ | $R^4$ | Metal halide |
|---|---|---|---|---|
| Me | Me | Me | $C_2H_4Cl$ | $ZnCl_2$ |
| Me | Me | Me | $C_2H_4Br$ | $ZnCl_2$ |
| Me | Me | Me | $C_2H_4OOCMe$ | $ZnCl_2$ |
| Me | Me | Me | $C_2H_4OH$ | $ZnCl_2$ |
| Me | Me | Me | $C_2HOHCl$ | $ZnCl_2$ |
| Me | Me | Me | $C_3H_7$ | $ZnCl_2$ |
| Me | Me | Me | $C_3H_6Br$ | $ZnCl_2$ |
| Me | Me | Me | $C_2H_4NH_2$ | $ZnCl_2$ |
| Me | Me | Me | $C_5H_{12}N^+ (CH_3)_3$ | $ZnCl_2$ |
| Me | Me | Me | $C_{10}H_{21}$ | $ZnCl_2$ |
| Et | Et | Et | $C_6H_{13}$ | $ZnCl_2$ |
| Et | Et | Et | $C_{12}H_{25}$ | $ZnCl_2$ |
| Me | Me | Me | $C_2H_4OOCMe$ | $ZnBr_2$ |
| Me | Me | Me | $C_2H_4OOCMe$ | $ZnBr_2$ |
| Me | Me | Me | $C_2H_4OOCMe$ | $ZnCl_2$ |
| Me | Me | Me | $C_2H_4OOCMe$ | $SnCl_2$ |
| Me | Me | Me | $C_2H_4OH$ | $ZnBr_2$ |
| Me | Me | Me | $C_2H_4OH$ | $FeCl_3$ |
| Me | Me | Me | $C_2H_4OH$ | $SnCl_2$ |
| Me | Me | Me | $C_2H_4OH$ | $ZnCl_2:SnCl_2$ (1:1). |

12. An ionic compound according to claim 1, wherein the ammonium salt comprises halide anions.

13. An ionic compound according to claim 1, in which the quaternary ammonium cation is chiral.

14. A method for preparing an ionic compound which method comprises reacting a quaternary ammonium compound of the formula:

$$R^1R^2R^3R^4N^+X^- \qquad (I)$$

or a mixture of two or more thereof;

with a halide of zinc, tin or iron, or a mixture of two or more thereof;

wherein $R^1$, $R^2$, and $R^3$, are each independently a $C_1$ to $C_5$ alkyl or a $C_6$ to $C_{10}$ cycloalkyl group, or wherein $R_2$ and $R_3$ taken together represent a $C_4$ to $C_{10}$ alkylene group, thereby forming with the N atom of formula I a 5 to 11-membered heterocyclic ring; and wherein $R^4$, is a $C_6$ to $C_{12}$ alkyl or a cycloalkyl group, or a $C_1$ to $C_{12}$ alkyl or a cycloalkyl group substituted with at least one group selected from OH, Cl, Br, F, I, $NH_2$, CN, $NO_2$, $COOR^5$, CHO, $COR^5$ and $OR^5$, wherein $R^5$ is a $C_1$ to $C_{10}$ alkyl or cycloalkyl group, and $X^-$ is a suitable counter-ion.

15. A method according to claim 14 in which molar ratio of the quaternary ammonium compound to the halide of zinc, tin, or iron is from 1:1 to 1:2.

16. A method according to claim 14, wherein the reaction is performed at temperature of at least 100° C.

17. A method of forming a solution comprising the step of dissolving a solute in an ionic compound according to claim 1.

18. A method of Friedel-Crafts acylation comprising the step of reacting an aromatic compound with an acid chloride in the presence of a catalytically effective amount of an ionic compound according to claim 1.

19. Diels-Alder reaction comprising the step of reacting a diene and a dienophile in an ionic compound according to claim 1.

20. An electrochemical cell containing an electrolyte comprising ionic compound according to claim 1.

* * * * *